United States Patent [19]

Albert et al.

[11] Patent Number: 5,686,410
[45] Date of Patent: Nov. 11, 1997

[54] POLYPEPTIDE DERIVATIVES

[75] Inventors: Rainer Albert, Basel; Wilfried Bauer, Lampenberg; Janos Pless, Basel, all of Switzerland

[73] Assignee: Novartis AG, Basel, Switzerland

[21] Appl. No.: 276,280

[22] Filed: Jul. 18, 1994

Related U.S. Application Data

[63] Continuation of Ser. No. 17,723, Feb. 16, 1993, abandoned, which is a continuation of Ser. No. 671,763, filed as PCT/EP90/01169 Jul. 12, 1990, abandoned.

[30] Foreign Application Priority Data

| | | | |
|---|---|---|---|
| Jul. 20, 1989 | [GB] | United Kingdom | 8916597 |
| Feb. 26, 1990 | [GB] | United Kingdom | 9004258 |
| Mar. 9, 1990 | [GB] | United Kingdom | 9005295 |

[51] Int. Cl.⁶ .................... A61K 38/18; C07K 14/485
[52] U.S. Cl. .................... 514/12; 514/2; 530/324
[58] Field of Search .................... 514/3, 12, 2; 530/324

[56] References Cited

U.S. PATENT DOCUMENTS

| | | |
|---|---|---|
| 4,824,986 | 4/1989 | Gansow . |
| 4,831,175 | 5/1989 | Gansow et al. . |
| 4,832,940 | 5/1989 | Ege . |
| 5,037,630 | 8/1991 | Fritzberg et al. . |
| 5,110,904 | 5/1992 | Haviv et al. . |

FOREIGN PATENT DOCUMENTS

| | | |
|---|---|---|
| 344724 | 5/1989 | European Pat. Off. . |
| 345723 | 6/1989 | European Pat. Off. . |
| WO89/12631 | 12/1989 | WIPO . |

OTHER PUBLICATIONS

Kovacs, M. et al., Effects of long–term administration of a superactive agonistic and an antagonistic GNRH analog on the pituitary–gonad, *Peptides* (Elmsford) 10, 925–932 (1989). See entire abstract.

Kuranov, I. et al., Amphibian bombesin and its analogue alytesin, *Biorg. Khim.* 15, 748–762 (1989). See entire abstract.

*Primary Examiner*—Paula K. Hutzell
*Assistant Examiner*—Benet Prickril
*Attorney, Agent, or Firm*—Joseph J. Borovian; Melvyn M. Kassenoff

[57] ABSTRACT

A biologically active peptide selected from growth factors, peptide hormones, interferons and cytokines and analogues and derivatives thereof, and bearing at least one chelating group linked to an amino group of said peptide, the chelating group being capable of complexing a detectable element and such amino group having no significant binding affinity to target receptors, are complexed with a detectable element and are useful as a pharmaceutical, e.g. a radiopharmaceutical for in vivo imaging of target tissues or for therapy.

17 Claims, No Drawings

POLYPEPTIDE DERIVATIVES

This is a continuation of application Ser. No. 08/017,723, filed Feb. 16, 1993, which in turn is a continuation of application Ser. No. 07/671,763, filed Mar. 18, 1991, both of which are now abandoned, application Ser. No. 07/671,763 being a 371 of PCT/EP90/01169, filed Jul. 12, 1990.

The present invention relates to polypeptides, a process for their production, their use as a pharmaceutical, e.g. for treatment of tumors or as in vivo diagnostic agents, and to novel intermediates therefor.

Over the years the presence of various receptors has been demonstrated in a variety of tumors. Diagnostic agents therefor often have no clearly defined structure. Thus radio-iodinated proteins or monoclonal antibodies having been reacted with chelating agents are randomly substituted. There thus exists a need for a new chemical approach to provide defined structures for use as diagnostic agents or for carrying radionuclides to tumors.

The present invention provides new labeled peptides useful in therapeutic and in vivo diagnostic applications.

According to the invention, there is provided a biologically active peptide selected from the group consisting of growth factors, peptide hormones, e.g. as indicated hereinafter, interferons and cytokines, e.g. IL-1, IL-4 or IL-6, and analogues or derivatives thereof and bearing at least one chelating group linked to an amino group of said peptide, the chelating group being capable of complexing a detectable element and such amino group having no significant binding affinity to target receptors.

These compounds are referred to thereafter as LIGANDS OF THE INVENTION. They possess at least one chelating group capable of reacting with a detectable element, e.g. a radionuclide, a radio-opaque element or a paramagnetic ion, to form a complex and further are capable of binding to receptors which are expressed or overexpressed by tumors or metastases. The chelating group is attached to an amino group of the peptide which is not involved in receptor binding. Such amino group with the attached chelating group does not significantly interfere with or prevent receptor binding of the peptide. Preferably said amino group is not directly attached to an aromatic residue.

The term receptors is used therein to cover also proto-oncogenes, e.g. HER-2/neu proto-oncogene (also known as c-erb B2) or EGFR (also known as c-erb B1) which are overexpressed e.g. in breast or ovarian cancer tumors.

According to the invention the chelating group may be attached either directly or indirectly by means of a divalent bridging group to the amino group of the peptide.

The term biologically active peptides is used therein to cover natural peptides isolated from nature or fermentation of cells, e.g. produced through genetic engineering, or synthesized and also their derivatives or analogues.

By derivatives and analogues is understood in particular natural peptides, wherein one or more amino acid units have been omitted and/or replaced by one or more other amino acid radical(s) and/or wherein one or more functional groups have been replaced by one or more other functional groups and/or wherein one or more groups have been replaced by one or several other isosteric groups. In general, the term covers all derivatives of a biologically active peptide which exhibit a qualitatively similar effect to that of the unmodified peptide. They may be for example more potent than the naturally occurring peptide. The term also covers antagonists to the naturally occurring peptide.

Preferably the biologically active peptide is of 3 or more than 3 amino-acids, in one or several linked chains. It is understood that the term biologically active peptide does not include anti-body or immunoglobulin molecules.

Suitable examples of growth factor peptides include epidermal growth factor (EGF), insulin-like growth factors (IGF-I and IGF-II), fibroblast growth factor (FGF), tumor necrosis factor (TNF), transforming growth factor (TGF-α and TGF-βn), platelet derived growth factor (PDGF), nerve growth factor, bombesin and analogues or derivatives thereof.

Suitable examples of hormonal peptides include insulin, LHRH, gastrin, gastrin releasing peptide, thyrotropin releasing hormone (TRH), thyroid stimulating hormone (TSH), prolactin, vasoactive intestinal polypeptide (VIP), angiotensin and analogues or derivatives thereof. Examples of cytokines are IL-1, IL-2, IL-4 and IL-6.

In a further or alternative embodiment, the present invention provides:

a. Epidermal growth factor (EGF may be of various origin, e.g. mouse EGF, rat EGF, human EGF);
b. Insulin-like growth factor (IGF), particularly IGF-1 (Somatomedin C);
c. LHRH, LHRH agonists or LHRH antagonists;
d. Gastrin;
e. Gastrin releasing peptide;
f. Bombesin or bombesin antagonists;
g. Transforming growth factors, particularly TGF-α;
h. Platelet derived growth factor;
i. Angiotensin;
j. Thyroid stimulating hormone;
k. Vasoactive intestinal polypeptide;
l. Fibroblast growth factor;
m. Prolactin;
n. Thyrotropin releasing hormone;
o. Insulin;
p. Tumor necrosis factor;
q. Nerve growth factor;
r. IL-1, IL-2, IL-4 or IL-6, preferably IL-1, IL-4 or IL-6;
s. Interferons and derivatives and analogues thereof
each of (a) to (s) bearing at least one chelating group linked to an amino group thereof, which amino group does not significantly participate in receptor binding and the chelating group being capable of complexing a detectable element.

In a series of specific or alternative embodiments, the present invention provides:

A. a peptide selected from any of the groups of peptides (a) to (q) as defined above and derivatives and analogues thereof each of (a) to (q) bearing at least one chelating group linked to an amino group of said peptide, which amino group does not significantly participate in receptor binding and the chelating group being capable of complexing a detectable element;

B. a peptide selected from any of the groups of peptides (a) to (l) as defined above and derivatives and analogues thereof each of (a) to (l) bearing at least one chelating group linked to an amino group of said peptide, which amino group does not significantly participate in receptor binding and the chelating group being capable of complexing a detectable element;

C. a peptide selected from any of the groups of peptides (a) to (k) as defined above and derivatives and analogues thereof each of (a) to (k) bearing at least one chelating group linked to an amino group of said peptide, which amino group does not significantly participate in receptor binding and the chelating group being capable of complexing a detectable element;

D. a peptide selected from any of the groups of peptides (a) to (g) as defined above and derivatives and analogues thereof each of (a) to (g) bearing at least one chelating group linked to an amino group of said peptide, which amino group does not significantly participate in receptor binding and the chelating group being capable of complexing a detectable element.

More particularly preferred peptides are EGF, LHRH, LHRH agonists, LHRH antagonists and bombesin antagonists.

The chelating group or groups present in the LIGAND OF THE INVENTION are linked covalently to the amino group of the peptide. Preferably the chelating group or groups present in the LIGAND OF THE INVENTION are attached, whether directly or indirectly, by an amide bond to the amino group of the peptide.

Preferably the LIGANDS OF THE INVENTION bear one chelating group.

According to the invention the chelating group may be attached either to a side chain amino group of the peptide, e.g. to the $N^\varepsilon$-amino group of a lysine, and/or to a terminal N-amino group of the peptide (referred to herein as $N^\alpha$-amino group), with the proviso that such amino group whether side chain or $N^\alpha$-attached does not significantly interfere with or impair the binding affinity of the peptide to the target receptors.

Among the peptides listed above, the following may preferably bear a chelating group on the $N^\alpha$-amino group: EGF, IGF-1, gastrin, gastrin releasing peptide, insulin, TGF-α, LHRH, bombesin, VIP, and analogues or derivatives thereof. Peptides which bear at least one chelating group attached to a side chain amino group preferably may be: an EGF comprising at least one lysine in its amino-acid sequence, e.g. hEGF, LHRH, LHRH agonists, LHRH antagonists, IGF-1, gastrin, gastrin releasing peptide, bombesin antagonists, VIP, and analogues or derivatives thereof.

A group of peptides comprises those wherein one lysine is present. Another group of peptides comprises those wherein more than one lysine group is present. A further group of peptides comprises those free of lysine.

As it will be appreciated when the peptide bears a terminal amino group which is substituted or protected, e.g. by acyl, the substituting or protecting group may conveniently be removed prior to the coupling with the chelating group or bridging group.

Suitable chelating groups are physiologically acceptable chelating groups capable of complexing a detectable element. Preferably the chelating group has substantially a hydrophilic character. Examples of chelating groups include e.g. iminodicarboxylic groups, polyaminopolycarboxylic groups, e.g. those derived from non cyclic ligands e.g. ethylene diaminetetraacetic acid (EDTA), diethylene triamine pentaacetic acid (DTPA), N-hydroxyethyl-N,N',N'-ethylene diaminetriacetic acid (HEDTA), ethylene glycol-O,O'-bis(2-aminoethyl)-N,N,N',N'-tetraacetic acid (EGTA), N,N'-bis(hydroxybenzyl)ethylenediamine-N,N'-diacetic acid (HBED) and triethylenetetramine hexaacetic acid (TTHA), those derived from substituted EDTA or -DTPA, those derived from macrocyclic ligands, e.g. 1,4,7,10-tetra-azacyclododecane-N,N',N",N'"-tetraacetic acid (DOTA), 1,4,8,11-tetraazacyclotetradecane-N,N',N",N'"-tetraacetic acid (TETA), C-functionalised tetraazacyclododecane-tetraacetic acids, tetraazacyclotetradecanetetra-acetic acids, triazacyclododecane triacetic acids and triazacyclononane triacetic acids, for example chelating groups derived from compounds of formula Ia, Ib or Ic,

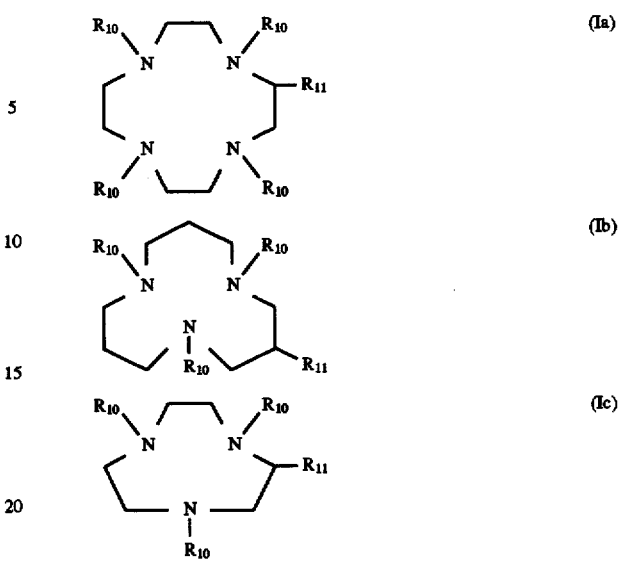

wherein
$R_{10}$ is —$CH_2COOH$ or a functional derivative thereof, e.g. an ester, and
$R_{11}$ is -Alk-$X_1$ or

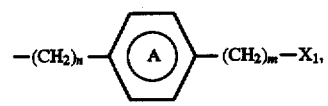

wherein each of n and m independently is 0, 1, 2 or 3, Alk is $C_{1-11}$alkylene, $X_1$ is —NCS or $NH_2$ optionally substituted by a protecting group and ring A is substituted or unsubstituted, those derived from N-substituted or C-substituted macrocyclic amines including also cyclames, e.g. as disclosed in EP 304, 780 A1 and in WO 89/01476-A, groups of formula IIa or IIb,

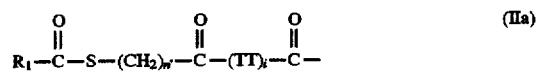

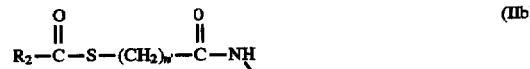

wherein
each of $R_1$, $R_2$ and $R_3$ independently is $C_{1-6}$alkyl, $C_{6-8}$aryl or $C_{7-9}$arylalkyl, each optionally substituted by OH, $C_{1-4}$alkoxy, COOH or $SO_3H$,

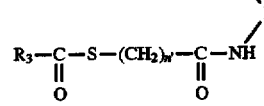

wherein the carbon atoms marked with * are attached to the imino groups,
n' is 1 or 2,
i is an integer from 2 to 6, and TT are independently α or β amino acids linked to each other by amide bonds, e.g. as disclosed in EP 247,866 A1 groups derived from bis-aminothiol derivatives, e.g. compounds of formula III

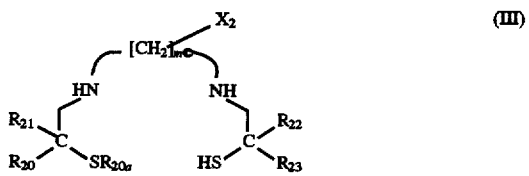

wherein
each of $R_{20}$, $R_{20a}$, $R_{21}$, $R_{22}$ and $R_{23}$ independently is hydrogen or $C_{1-4}$alkyl, $X_2$ is either a group capable of reacting with the N-amino group of the peptide, or a group capable of binding with the divalent bridging group and m' is 2 or 3, groups derived from dithiasemicarbazone derivatives, e.g. compounds of formula IV

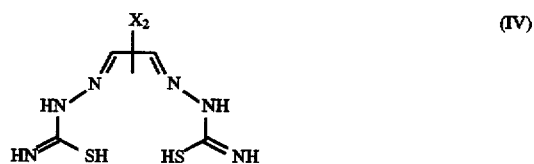

wherein
$X_2$ is as defined above,
groups derived from propylene amine oxime derivatives, e.g. compounds of formula V

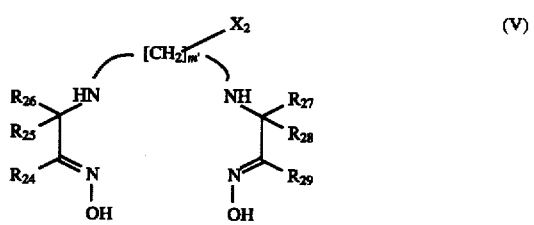

wherein
each of $R_{24}$, $R_{25}$, $R_{26}$, $R_{27}$, $R_{28}$ and $R_{29}$ independently are hydrogen or $C_{1-4}$alkyl, and
$X_2$ and m' are as defined above, groups derived from diamide dimercaptides, e.g. compounds of formula VI

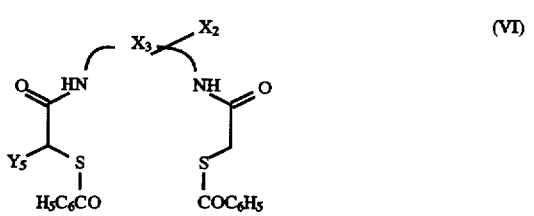

wherein
$X_2$ is as defined above,
$X_3$ is $C_{1-4}$alkylene, $C_{1-4}$alkylene substituted by one or two $CO_2R_{30}$, by $CH_2COR_{30}$, $CONH_2$ or $CONHCH_2CO_2R_{30}$, phenylene, or phenylene substituted by $CO_2R_{30}$ wherein $R_{30}$ is $C_{1-4}$alkyl, and
$Y5$ is hydrogen or $CO_2R_{30}$,
groups derived from porphyrins, e.g. N-benzyl-5,10,15,20-tetra-kis-(4-carboxyphenyl)porphine or TPP bearing a group $X_2$ as defined above, or from Desferal (Deferoxamine).

The contents of all the above publications including the specific compounds are specifically incorporated herein by reference.

Aryl is preferably phenyl. Arylalkyl is preferably benzyl. Alkylene may be straight chain or branched, preferably straight chain.

Examples of $X_2$ include radicals of formula $-(X_4)_{n''}-X_5$ wherein $X_4$ is $C_{1-6}$alkylene; $C_{1-6}$alkylene optionally attached to the carbon atom by an oxygen atom or —NH— or phenyl-$C_{1-3}$alkyl; n" is 0 or 1 and $X_5$ is —NCS, —NCO, or a carboxy group or a functional derivative thereof, e.g. acid halide, anhydride or hydrazide. When $X_4$ is phenyl-$C_{1-3}$alkyl, $X_5$ is preferably in para. For example $X_2$ can be —O—$(CH_2)_{2-6}$—COOH or a functional derivative thereof, or p-isothiocyanato-benzyl or -phenethyl.

In compounds of formula Ia, Ib or Ic $R_{11}$ is preferably Alk-NCS or

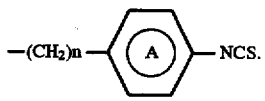

Preferably Alk is $C_{1-6}$ alkylene, more preferably $C_{1-4}$alkylene, n is preferably 1 or 2. Ring A is preferably unsubstituted.

In compounds of formula III, $R_{20a}$ is preferably hydrogen.
In compounds of formula V, $R_{24}$ and/or $R_{29}$ are preferably hydrogen. Each of $R_{25}$ to $R_{28}$ independently is preferably methyl. More preferably $R_{25}$ to $R_{28}$ are each methyl. m' is preferably 3. When m' is 3, $X_2$ is preferably located in position 2.

$X_2$ is preferably p-isothiocyanato-benzyl or p-isothiocyanatophenethyl.

Particularly preferred chelating groups are those derived from
EDTA, DTPA, DOTA; or
substituted EDTA or DTPA, e.g. N'-p-isothiocyanatobenzyldiethylene triamine-N,N,N'',N'''-tetraacetic acid, N'-p-isothiocyanatophenethyl-diethylene triamine-N,N,N'',N'''-tetraacetic acid, N-{2-[bis(carboxymethyl)amino]ethyl}-N'-{2-[bis(carboxymethyl)amino]-2-(p-isothiocyanatobenzyl)-ethyl}-glycine or -(P-isothiocyanatophenethyl)-homologue; or
substituted DOTA, e.g. a compound of formula Ia, or compounds of formula Ib or Ic, particularly those wherein $R_{11}$ is —$(CH_2)_{1-6}$—NCS, p-isothiocyanatobenzyl or p-isothiocyanatophenethyl; or
compound of formula Va

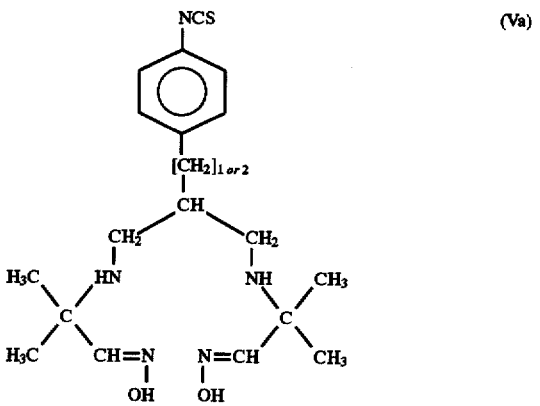

As will be appreciated, where the chelating group present in the LIGAND OF THE INVENTION contains vicinal carboxylic acid groups, these may also be present as anhydride functional groups.

According to the invention when the chelating group is attached indirectly by means of a divalent bridging group or a spacer group to an amino group of the peptide, it may be linked for example through a group of formula ($\alpha_1$)

$$-Z-R-CO- \quad (\alpha_1)$$

wherein

R is $C_{1-11}$alkylene, hydroxy substituted $C_{2-11}$alkylene, $C_{2-11}$alkenylene,

cyclohexylene, substituted cyclohexylene, or a radical of formula ($\alpha_2$)

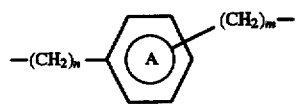

wherein n and m are as defined above, the ring A is substituted or unsubstituted, and $R_5$ is a residue as attached in C$\alpha$ of a natural or synthetic $\alpha$-amino acid, and Z is a divalent group derived from a functional moiety capable of covalently reacting with the chelating agent.

Preferably R is $C_{1-4}$alkylene, —CH($R_5$)— or a radical of formula ($\alpha_2$) wherein ring A is unsubstituted.

In the radical of formula ($\alpha_2$), the substituent —(CH$_2$)$_m$— is preferably located in meta or para, more preferably in para.

Z may be for example a group which can form an ether, ester or amide bonding with the chelating group. Z is preferably —CO— or —NH—, more preferably —NH—.

When Z is —CO—, the divalent bridging group of formula ($\alpha_1$) may be a divalent radical derived from a dicarboxylic acid.

Examples of significances for $R_5$ include e.g. hydrogen, $C_{1-11}$alkyl, benzyl, substituted benzyl, e.g. substituted on the phenyl ring by hydroxy, halogen, $C_{1-3}$alkyl or $C_{1-3}$alkoxy, and —CH$_2$-naphthyl.

A group of preferred LIGANDS OF THE INVENTION are the compounds of formula X $$A-Z_1-B \quad (X)$$

wherein

A is a chelating group, for example a chelating group derived from a chelating agent comprising a reactive carboxy or amino group or a functional derivative thereof, $Z_1$ is a direct bond or a divalent bridging group, and B is a biologically active peptide, preferably a peptide (a) to (s) or an analogue or derivative thereof as defined above, the moiety A—Zx— being attached to an amino group of B having no significant binding affinity to target receptors.

Preferred compounds of formula X are those wherein:

A is a chelating group derived from N'-p-isothiocyanatobenzyldiethylene triamine-N,N,N",N"-tetraacetic acid, N'-p-isothiocyanatophenethyl-diethylene triamine-N,N,N",N"-tetraacetic acid, N-{2-[bis(carboxymethyl)amino]ethyl}-N'-{2-[bis(carboxy-methyl) amino]- 2-(p-isothiocyanatobenzyl)-ethyl}-glycine, DOTA, C-functionalised tetraazacyclododecane-tetraacetic acids, C-functionalised tetraazacyclotetradecane-tetraacetic acids, C-functionalised triazacyclododecane triacetic acids, C-functionalised triazacyclononane triacetic acids, preferably compounds of formula Ia, Ib or Ic, particularly compounds of formula Ia, Ib or Ic wherein $R_{11}$ is —(CH$_2$)$_{1-6}$—NCS, p-isothiocyanatobenzyl or p-isothiocyanatophenethyl, or from a compound of formula V

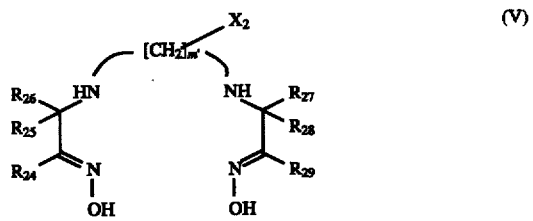

wherein $R_{24}$ to $R_{29}$ and m' are as defined above, and $X_2$ is p-isothiocyanato-benzyl or -phenethyl; or $Z_1$ is a direct bond or a group of formula $\alpha_1$ wherein the —CO— group is attached to the amino group of the peptide and Z is —NH—; or B is EGF, LHRH, a LHRH agonist, a LHRH antagonist, bombesin or a bombesin antagonist.

Examples of LHRH antagonists are compounds of formula VII $$R_{33}-A_1-B_1-C_1-D_1-E_1-F_1-G_1-H_1-I_1-K_1-NH_2 \quad (VII)$$

wherein $R_{33}$ is hydrogen, $C_{1-7}$acyl or carbamoyl, $A_1$ is D-Phe optionally substituted in the phenyl ring by halogen, CF$_3$, $C_{1-3}$alkyl and/or $C_{1-3}$alkoxy, $\alpha$- or $\beta$-naphthyl-D-alanine, D-Trp optionally substituted in 5 or 6 position by halogen or $C_{1-3}$alkoxy and/or in 1 position by formyl or acetyl, D- or L- Pro, D- or L-3,4-dehydroproline, D- or L-Ser, D- or L-Thr, D- or L-Ala, D-pyroglutamine, 3-(9-anthryl)-D,L-alanyl, 3-(2-fluorenyl)-D,L-alanyl or 3-(Het)-D,L-alanyl wherein Het is a heterocyclic aryl radical selected from

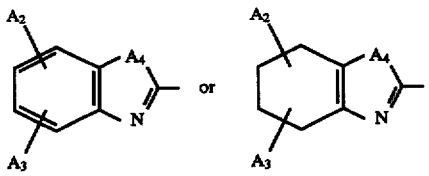

wherein $A_2$ and $A_3$ are independently selected from the group consisting of hydrogen, $C_{1-4}$alkyl, chlorine and bromine, and $A_4$ is O, S or N $B_1$ is D-Phe optionally substituted in the phenyl ring by halogen, NO$_2$, $C_{1-3}$alkyl or $C_{1-3}$alkoxy, D-$\alpha$-methylPhe optionally substituted in 4 position by chlorine, 2,2-diphenylglycine or 3-(2-naphthyl)-D-alanine, $C_1$ is D-Trp optionally substituted in 5 or 6 position by halogen, NO$_2$ or $C_{1-3}$alkoxy and/or in 1 position by formyl or acetyl, 3-(2- or 1-(naphthyl)-D-alanine, 3-D-pyridylalanine, D-Tyr, D-Phe optionally substituted by halogen, $C_{1-3}$alkyl and/or $C_{1-3}$alkoxy, D,3-Pz-Ala, D-Tin-Glu or D-Nic-Lys, $D_1$ is L-Ser, $E_1$ is Tyr, Phe optionally substituted in the phenyl ring by halogen, $C_{1-3}$alkyl and/or $C_{1-3}$alkoxy, Orn, Lys, Lys-Nic, MPic-Lys, Pic-Lys, DPic-Lys, MPic-Lys, DMG-Lys, Pmc-Lys, Pzc-Lys, PmACAla, PzACAla, His, Dpo, Arg, 3-(3-pyridyl)-Ala, Trp, N-(3-pyridyl)acetyl-Lys or Glu(pMeO-phenyl), Cit, HOBLys or PzACAla, $F_1$ is D-Phe optionally substituted in the phenyl ring by halogen, $NO_2$, $NH_2$, $C_{1-3}$alkyl or $C_{1-3}$alkoxy, D-Trp optionally substituted in 5 or 6 position by halogen, $NO_2$ and/or $C_{1-3}$alkoxy and/or in 1 position by formyl or acetyl, 3-(2-naphthyl)-L-alanyl, D-Tyr, D-Orn, D-Lys, D-Lys-Nic, D-MNic-Lys, D-MPic-Lys, Pic-Lys, DPic-Lys, D-Pmc-Lys, D-Pzc-Lys, D-Bz-Lys, D-ILys, AnGlu, D-NACAla, D-PzACAla, D-PmACAla, D-3-(3-pyridyl)-Ala, D-His (subst. H or benzyl), D-Arg, D-homo-Arg(Et$_2$), D-Cit, D-HCi, D-Lys-Pic, D-Cit($C_{1-3}$-alkyl), D-HCi($C_{1-3}$alkyl), D-Glu(AA) or α-amino-ω-ureido-$C_{2-4}$alkanoic acid, $G_1$ is Leu, Nle, Nval, N-α-methylLeu, Trp, Phe, Met, Tyr, Val, Ile, alloIle, Abu or Ala, $H_1$ is Arg, IOrn, Lys, ILys or Cyp-Lys $I_1$ is Pro, hydroxyproline, 3,4-dehydroproline, Pip and $K_1$ is D-Ala, D-Leu, Gly, D-Ser or Sar, in free form or in salt form.

The chelating group or groups may be attached to the terminal $N^\alpha$-amino group in position 1 when $R_{33}$ is hydrogen and/or to the free amino groups present in $E_1$ and/or $F_1$ and/or $H_1$ of formula VII. Preferably the LIGANDS OF THE INVENTION of the LHRH antagonist series are compounds of formula VII comprising a chelating group attached to the amino group in position 1 or 6 or 8, particularly 6 or 8.

Examples of LHRH agonists are compounds of formula VIII

pGlu-His-A$_5$-Ser-B$_2$-C$_2$-D$_2$-Arg-Pro-E$_2$ (VIII)

in which $A_5$ is Trp, Phe or 3-(1-naphthyl)Ala, $B_2$ is Tyr, Phe D-Trp, or 3-(pentafluorophenyl)Ala, $C_2$ is an amino-acid unit of formula

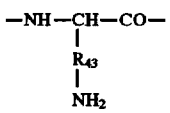

wherein $R_{34}$ is —(CH$_2$)$_{p'}$—, —(CH$_2$)$_{p''}$—CO—, —(CH$_2$)$_{p''}$—R$_{35}$— or —(CH$_2$)$_{p''}$—Y$_6$—(CH$_2$)$_{p'''}$—, wherein p' is 1 to 5, p" is 0 or 1 to 3, each of p'" independently is 1 to 3, $R_{35}$ is phenyl or cyclohexyl and $Y_6$ is O, S, —SO— or SO$_2$, $D_2$ is Leu, Ile, Nle, MeLeu, and $E_2$ is Gly-NH$_2$, —NH—R$_{31}$ or —NH—NH-CO—NH—R$_{32}$ wherein $R_{31}$ is hydrogen, lower alkyl, cycloalkyl or fluoro lower alkyl and $R_{32}$ is hydrogen or lower alkyl, in free form or in salt form.

The residue $C_2$ has preferably the D-configuration. The chelating group is preferably attached to the free amino group present in $C_2$.

Examples of bombesin antagonists are compounds e.g. as disclosed in EP 339,193 A and EP 315,367 A, the contents of which being herein incorporated by reference, particularly compounds of formula IXa

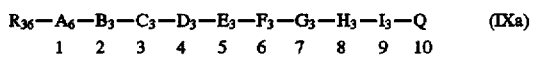

$R_{36}$—A$_6$—B$_3$—C$_3$—D$_3$—E$_3$—F$_3$—G$_3$—H$_3$—I$_3$—Q (IXa)
 1    2    3    4    5    6    7    8    9   10 wherein $R_{36}$ is hydrogen, $C_{1-6}$alkyl, $C_{2-6}$alkanoyl, $C_{4-6}$cycloalkoxycarbonyl or $C_{1-4}$alkoxycarbonyl, $A_6$ is a direct bond or Gly, Arg, Lys, Phe, Asp, Nal, Pro, β-Ala or Glp, $B_3$ is a direct bond or Gly, Pro or Asn, $C_3$ is a direct bond or Lys or D-Nal, $D_3$ is a direct bond or His, MeHis, EtHis, PrHis, Gln, Glu(OMe)-Glp, Leu, MeLeu, Lys, Pal, Phe, Pro, Arg, Trp or Thr, $E_3$ is Trp, Val, Nal, Leu, Lys, Pal, $F_3$ is Ala, MeAla, Aib, Gly, Pro, Leu, Phe, Ser, Val, Nal, Thr, Arg or Glu, $G_3$ is Val, Aib, Leu, Ile, Thr, Phe or Ser, $H_3$ is Gly, Sat, Ala, Ser, Aib, Pro, Lys, Asp, Arg, Val, Ac$^3$c, Ac$^5$c or Ac$^6$c, $I_3$ is His, MeHis, Aib, Val, Leu, MeLeu, Ala, Ile, Met, Pro, Phe, Gln, Lys, Pal, Ser, Thr, Glu, Asp, Trp or Nal, and Q is $K_3$-$R_{37}$ wherein $K_3$ is Leu, MeLeu, Ile, MeIle, Aib, Pro, Val, MeVal, Phe, Ape, MeApe, Met, Ser, Gln, Glu or Trp and $R_{37}$ is $C_{1-3}$alkylamino, $C_{1-4}$(dialkyl)amino or $C_{1-3}$alkoxy or Q is $C_{1-6}$alkoxy, $C_{1-10}$alkylamino or $C_{1-10}$(dialkyl)amino, and compounds of formula IXb

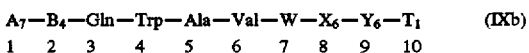

A$_7$—B$_4$—Gln—Trp—Ala—Val—W—X$_6$—Y$_6$—T$_1$ (IXb)
 1    2    3    4    5    6   7   8    9   10 wherein $A_7$ is hydrogen, Boc, Lys, Arg, $B_4$ is a direct bond or Ash, Thr, Glp, W is Gly or Ala, $X_6$ is a direct bond, His($R_{38}$), Phe, Ser or Ala, $Y_6$ is a direct bond, Leu or Phe, $T_1$ is amino, NH(CH$_2$)$_4$CH$_3$, benzylamino, Met-$R_{39}$, Leu-$R_{39}$, Ile-$R_{39}$, Ile-$R_{39}$ or Nle-$R_{39}$, $R_{38}$ is hydrogen or benzyl, and $R_{39}$ is amino, hydroxy, methoxy or —NHNH$_2$, in free form or in salt form.

Preferably the LIGANDS OF THE INVENTION of the bombesin antagonist series are compounds of formula IXa or IXb comprising a chelating group attached to the free amino group or groups when present in position 1, and/or 2 and/or 4 and/or 5, and/or 6 and/or 7 and/or 8, more preferably only one chelating group attached as indicated above.

The LIGANDS OF THE INVENTION may exist e.g. in free or salt form. Salts include acid addition salts with e.g. organic acids, polymeric acids or inorganic acids, for example hydrochlorides and acetates, and salt forms obtainable with the carboxylic or sulphonic acid groups present in the chelating group, e.g. alkali metal salts such as sodium or potassium, or substituted or unsubstituted ammonium salts.

The present invention also includes a process for the production of the LIGANDS OF THE INVENTION, comprising a) removing at least one protecting group which is present in a peptide bearing a chelating group, or b) linking together by an amide bond two peptide fragments each of them containing at least one amino acid in protected or unprotected form and one of them containing the chelating group, wherein the amide bond is in such a way that the desired amino acid sequence is obtained, and then effecting optionally stage a) of the process, or c) linking together a chelating agent and the desired peptide in protected or unprotected form in such a way that the chelating group is fixed on the desired amino group of the peptide, and then effecting optionally stage a), or d) removing a functional group of an unprotected or a protected peptide bearing a chelating group or converting it into another functional group so that another unprotected or a protected peptide bearing a chelating group is obtained and in the latter case effecting stage a) of the process, and recovering the LIGAND thus obtained in free form or in salt form.

The above reactions may be effected in analogy with known methods, e.g. as described in the following examples, in particular process a). When the chelating group is attached by an ether, ester or amide bond, this may be carried out analogously to the methods used for ether, ester or amide formation respectively. Where desired, in these reactions, protecting groups which are suitable for use in peptides or for the desired chelating groups may be used for functional groups which do not participate in the reaction. The term protecting group may also include a polymer resin having functional groups.

In the above process steps b) and c), when it is desired to produce a peptide in which the chelating group is attached by means of a divalent bridging or spacer group to the amino group of the peptide, the bridging group may be present on the corresponding amino-acids, peptide fragments or peptides used as starting material, or attached to the chelating group. Said amino-acids, peptide fragments or peptides may be prepared by reacting in analogy with known methods the corresponding amino-acids or peptides free of bridging or spacer group with a corresponding bridging or spacer-yielding compound, for example an acid of formula HO—CO—R—COOH, H$_2$N—R—COOH or a reactive acid derivative thereof such as an active ester. Examples of active ester groups or carboxy activating groups are e.g. 4-nitrophenyl, pentachlorophenyl, pentafluorophenyl, succinimidyl or 1-hydroxy-benzotriazolyl.

Alternatively the chelating agent may first be reacted with a bridging or spacer group-yielding compound, in order to bear the bridging or spacer group and then be reacted in analogy with known methods with the peptide, peptide fragment or amino-acid. According to a preferred embodiment of the invention, when the chelating group is derived from a polyamino polycarboxylic compound, the chelating agent, e.g. EDTA- or DTPA-dianhydride, is reacted with the bridging or spacer-group yielding compound, e.g. H$_2$N—R—COOH or a reactive acid derivative thereof, for example an alkyl ester thereof, to yield the chelating agent modified by the bridging group. This compound may then be activated, e.g. converted into the corresponding hydrazide by reaction of the modified chelating agent with e.g. hydrazine hydrate. The hydrazide chelating agent may then be reacted with the amino-acid, peptide fragment or peptide in analogy with known methods, e.g. via azide coupling after conversion into the corresponding azide.

According to a further preferred embodiment of the invention, when it is desired to link a chelating agent bearing a carboxylic function, e.g. —COOH or an anhydride thereof, directly to the amino group of the peptide (in the absence of a divalent bridging or spacer group), the chelating agent may be activated, e.g. converted into the corresponding hydrazide by reaction with e.g. hydrazine hydrate. The hydrazide chelating agent may then be reacted with the amino-acid, peptide fragment or peptide in analogy with known methods, e.g. via azide coupling after conversion into the corresponding azide.

When it is desired to attach the chelating group to the terminal N-amino group of a peptide or peptide fragment used as starting material, and which comprises one or more side chain amino groups, these side chain amino groups are conveniently protected with a protecting group, e.g. as used in peptide chemistry.

When it is desired to attach the chelating group on a side chain amino group of a peptide or peptide fragment used as starting material, and the peptide comprises a free terminal amino group, the latter may be protected with a protecting group.

When it is desired to attach the chelating group on the terminal amino group of a peptide or peptide fragment used as starting material, and said terminal amino group is substituted or in a protected form, e.g. substituted by acyl, the substituting or protecting group may conveniently be removed prior to the coupling with the chelating group.

The chelating groups of formula IIa or IIb may be linked to a peptide by reacting a chelating agent of formula II'a or II'b,

 (II'a)

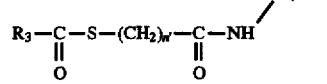 (II'b)

wherein X is an activating group capable of forming an amide bond. The reaction may be performed as disclosed e.g. in EP 247,866 A$_1$.

The chelating agent used in process step b) or c) may be known or prepared in analogy with known procedures.

The LIGANDS OF THE INVENTION may be purified in conventional manner, e.g. by chromatography. Preferably the LIGANDS OF THE INVENTION contain less than 5% by weight of peptides free of chelating groups.

In a further embodiment the present invention also provides the LIGANDS OF THE INVENTION as defined above which are complexed with a detectable element (hereinafter referred to as CHELATES OF THE INVENTION), in free form or in salt form, their preparation and their use for in vivo diagnostic and therapeutic treatment.

The CHELATES OF THE INVENTION comprise each LIGAND OF THE INVENTION, particularly as mentioned in (a) to (s) above, complexed with a detectable element.

In a series of specific or alternative embodiment, the present invention provides also the groups of LIGANDS as specified in (A) to (D) above complexed with a detectable element.

By detectable element is meant any element, preferably a metal ion which exhibits a property useful in therapeutic or in vivo diagnostic techniques, e.g. emission of a detectable radiation or an influence on NMR relaxation properties.

Suitable detectable metal ions include for example heavy elements or rare earth ions, e.g. as used in CAT scanning (Computer axial tomography), paramagnetic ions, e.g. $Gd^{3+}$, $Fe^{3+}$, $Mn^{2+}$ and $Cr^{2+}$, fluorescent ions e.g. $Eu^{3+}$, and radionuclides, e.g. γ-emitting radionuclides, β-emitting radionuclides, α-emitting radionuclides, positron-emitting radionuclides e.g. $^{68}Ga$, $^{62}Cu$, $^{52}Fe$ and $^{62}Zn$ and Auger-electron-emitting radionuclides.

Suitable γ-emitting radionuclides include those which are useful in diagnostic techniques. The γ-emitting radionuclides advantageously have a half-life of from 1 hour to 40 days, preferably from 5 hours to 4 days, more preferably from 12 hours to 3 days. Examples are radionuclides derived from Gallium, Indium, Technetium, Ytterbium, Rhenium and Thallium e.g. $^{67}$Ga, $^{111}$In, $^{99m}$Tc, $^{169}$Yb and $^{186}$Re. Preferably the γ-radionuclide is selected depending on the metabolism of the selected LIGAND OF THE INVENTION or the peptide used. More preferably the LIGAND OF THE INVENTION is chelated with a γ-radionuclide having a half-life corresponding to or longer than the half-life of the peptide on the tumor.

Further radionuclides suitable for use in imaging are positron-emitting radionuclides, e.g. as mentioned above.

Suitable β-emitting radionuclides include those which are useful in therapeutic applications, for example those derived from $^{90}$Y, $^{67}$Cu, $^{186}$Re, $^{188}$Re, $^{169}$Er, $^{121}$Sn, $^{127}$Te, $^{149}$Pr, $^{198}$Au, $^{109}$Pd, $^{165}$Dy, $^{32}$P, $^{142}$Pr or Ag. The β-radionuclide advantageously have a half-life of from 1 hr to 14.3 days, preferably from 2.3 to 100 hrs. Preferably the β-emitting radionuclide is selected in order to have a half-life corresponding to or longer than the half-life of the peptide on the tumor.

Suitable α-emitting radionuclides are those which are used in therapeutic treatments, e.g. $^{211}$At, $^{212}$Bi.

Further radionuclides suitable for therapeutic treatment are Auger-electron-emitting radionuclides, e.g. $^{125}$I, $^{123}$I, $^{77}$Br.

The CHELATES OF THE INVENTION may be prepared by reacting the LIGAND with a corresponding detectable element yielding compound, e.g. a metal salt, preferably a water-soluble salt. The reaction may be carried out by analogy with known methods, e.g. as disclosed in Pertin, Organic Ligand, Chemical Data Series 22. NY Pergamon Press (1982); in Krejcarit and Tucker, Biophys. Biochem. Res. Com. 77:581 (1977) and in Wagner and Welch, J. Nucl. Med. 20: 428 (1979).

The CHELATE may conveniently be formed by reacting the LIGAND with the detectable element yielding compound at a pH at which the LIGAND OF THE INVENTION is chemically stable.

The detectable metal ion may also be provided to the solution as a complex with an intermediate chelating agent, e.g. a chelating agent which forms a chelate complex that renders the metal ion soluble but is less thermodynamically stable than the CHELATE. Example of such an intermediate chelating agent is 4,5-dihydroxy-1,3-benzene-disulfonic acid (Tiron). In such a process, the detectable metal ion exchanges the ligand.

The CHELATES OF THE INVENTION may also be produced by linking together covalently a chelating agent complexed with the detectable element, and the peptide in protected or unprotected form and if desired removing at least one protecting group which is present. The same reaction may be performed using a chelating agent complexed with a metal ion and then in the resulting complexed peptide the metal ion may be replaced by the desired detectable element.

The CHELATES OF THE INVENTION may also be produced by linking together a chelating agent complexed with the detectable element, and a peptide fragment comprising at least one amino acid in protected or unprotected form and then continuing the peptide synthesis step by step until the final peptide sequence is obtained and if desired removing at least one protecting group which is present. Instead of the detectable element the chelating agent may be complexed with a non detectable metal and this metal may then be replaced by the detectable element in the resulting complexed peptide.

According to the invention the chelating group may be attached through a bridging or spacer group, e.g. a radical of formula ($\alpha_1$) as defined above; in such a case it is meant in the above process steps for preparing the CHELATES OF THE INVENTION that either the peptide or peptide fragment or the chelating agent may bear said bridging or spacer group.

The above mentioned reactions may be effected in analogy to known methods. Depending on the chelating group present, the labeling efficiency may approach 100% so that purification is not required. Radionuclides such as for example Technetium-99m may be used in oxidized form, e.g. Tc-99m pertechnetate, which may be complexed under reducing conditions.

The above mentioned reactions are conveniently effected under conditions avoiding trace metal contamination. Preferably distilled de-ionized water, ultrapure reagents, chelation-grade radioactivity etc. are used to reduce the effects of trace metal.

The CHELATES OF THE INVENTION may exist e.g. in free or salt form. Salts include acid addition salts with e.g. organic acids, polymeric acids or inorganic acids, for example hydrochlorides and acetates, and salt forms obtainable with the carboxylic acid groups present in the molecule which do not participate to the chelate formation, e.g. alkali metal salts such as sodium or potassium, or substituted or unsubstituted ammonium salts.

Particularly preferred CHELATES OF THE INVENTION are:

compounds of formula X wherein A is a chelating group derived from a compound of formula Va, said compounds of formula X being complexed with radioactive Tc, e.g. $^{99m}$Tc;

compounds of formula x wherein A is a chelating group derived from a compound of formula Ia, Ib or Ic wherein $R_{11}$ is —(CH$_2$)$_{1-6}$—NCS, p-isothiocyanatobenzyl or p-isothiocyanatophenethyl, said compounds of formula X being complexed with radioactive Yttrium, e.g. $^{90}$Y;

compounds of formula X wherein A is a chelating group derived from N'-p-isothiocyanatobenzyl-diethylene triamine-N,N,N",N"-tetraacetic acid or N'-p-isothiocyanatophenethyldiethylene triamine-N,N,N", N"-tetraacetic acid, said compounds of formula X being complexed with Europium;

compounds of formula X wherein A is a chelating group derived from N-{2-bis(carboxymethyl)amino]ethyl}-N'-{2-[bis(carboxymethyl)amino]-2-(p-isothiocyanatobenzyl)-ethyl}-glycine, said compounds being complexed with radioactive Indium or Yttrium, e.g. $^{90}$Y or $^{111}$In.

The CHELATES OF THE INVENTION and their pharmaceutical acceptable salts exhibit pharmaceutical activity and are therefore useful depending on the detectable metal ion either as an imaging agent, e.g. visualisation of receptor-positive tumors and metastases when complexed with a paramagnetic, a γ-emitting metal ion or a positron-emitting radionuclide, or as a radiopharmaceutical for the treatment in vivo of receptor-positive tumors and metastases when complexed with a α- or β-radionuclide or an Auger-electron-emitting radionuclide, as indicated by standard tests, e.g. showing a biodistribution as indicated in Example 12 on i.v. administration of from about 1 to 5 μg/kg of LIGAND labeled with 0.5 to 2 mCi $^{111}$In. The CHELATES OF THE INVENTION also possess affinity for receptors expressed or overexpressed by tumors and metastages, as indicated in standard in vitro binding assays, e.g. as described in Example 11, the CHELATES being preferably added at a concentration of about $10^{-10}$ to $10^{-8}$M.

In a series of specific or alternative embodiments, the present invention also provides:

1. A method for in vivo imaging, e.g. in vivo detection of tumors or metastases in a subject which comprises a) administering a CHELATE OF THE INVENTION to said subject and b) recording the localisation of the tissues, e.g. tumors or metastases, targeted by said CHELATE.

This method of the invention is particularly useful for the in vivo detection of tumors which express or overexpress receptors, more particularly at a high incidence on tumorigenic cells. CHELATES OF THE INVENTION for use in the in vivo detection method of the invention are the CHELATES which are complexed with a γ-emitting radionuclide, a positron-emitting radionuclide or a paramagnetic metal ion, e.g. as indicated above.

The CHELATES OF THE INVENTION for use as an imaging agent in method (1) may be administered parenterally, preferably intravenously, e.g. in the form of injectable solutions or suspensions, preferably in a single injection. An appropriate dosage will of course vary depending upon, for example, the LIGAND and the type of detectable element used, e.g. the radionuclide. A suitable dose to be injected is in the range to enable imaging by photoscanning procedures known in the art. When a radiolabeled CHELATE OF THE INVENTION is used, it may advantageously be administered in a dose having a radioactivity of from 0.1 to 50 mCi, preferably 0.1 to 30 mCi, more preferably 0.1 to 20 mCi.

In animals an indicated dosage range may be of from 0.1 to 10 μ/kg of LIGAND labeled with 0.1 to 2 mCi γ-emitting radionuclide, e.g. $^{111}$In. In larger mammals, for example humans, an indicated dosage range may be of from 1 to 200 μg LIGAND labeled with 0.1 to 15 mCi, preferably 0.1 to 30 mCi, e.g. 3 to 15 mCi, γ-emitting radionuclide, depending on the γ-emitting radionuclide used. For example with In, it is preferred to use a radioactivity in the lower range, whereas with Tc, it is preferred to use a radioactivity in the upper range.

The enrichment in the tumorigenic sites with the CHELATES may be followed by the corresponding imaging techniques, e.g. using nuclear medicine imaging instrumentation, for example a scanner, γ-camera, rotating γ-camera, each preferably computer assisted; PET-scanner (Positron emission tomography); MRI equipment or CAT scanning equipment.

2. A method for in vivo treatment of tumors and metastases in a subject in need of such a treatment which comprises administering to said subject a therapeutically effective amount of a CHELATE OF THE INVENTION.

CHELATES OF THE INVENTION for use in the in vivo treatment method of the invention are the CHELATES complexed with a α-, β- or Auger-electron-emitting radionuclide as defined above.

The method of the invention is particularly useful for in vivo treatment of tumors which express or overexpress receptors, more particularly at a high incidence on tumorigenic cells.

Dosages employed in practising the therapeutic method of the present invention will of course vary depending e.g. on the particular condition to be treated, for example the volume of the tumor, the particular CHELATE employed, for example the half-life of the CHELATE in the tumor, and the therapy desired. In general, the dose is calculated on the basis of radioactivity distribution to each organ and on observed target uptake. For example the CHELATE may be administered at a daily dosage range having a radioactivity of from 0.1 to 3 mCi/kg body weight, e.g. 1 to 3 mCi, preferably 1 to 1.5 mCi/kg body weight.

In animals an indicated dosage range may be of from 0.1 to 5 μ/kg of LIGAND labeled with 0.1 to 3 mCi α- or β-emitting radionuclide, e.g. $^{90}$Y. In larger mammals, for example humans, an indicated dosage range is of from 1 to 200 μg LIGAND labeled with 0.1 to 3 mCi/kg body weight, e.g. 0.1 to 1.5 mCi/kg body weight α- or β-emitting radionuclide, conveniently administered in divided doses up to 4 times a day.

The α- or β-emitting CHELATES OF THE INVENTION may be administered by any conventional route, in particular parenterally, e.g. in the form of injectable solutions or suspensions. They may also be administered advantageously by infusion, e.g. an infusion of 30 to 60 min. Depending on the site of the tumor, they may be administered as close as possible to the tumor site, e.g. by means of a catheter. The mode of administration selected may depend on the dissociation rate of the CHELATE used and the excretion rate.

The CHELATES OF THE INVENTION may be administered in free form or in pharmaceutically acceptable form. Such salts may be prepared in conventional manner and exhibit the same order of activity as the free compounds.

The CHELATES OF THE INVENTION for use in the method of the present invention may preferably be prepared shortly before the administration to a subject, i.e. the labeling with the desired detectable metal ion, particularly the desired α-, β- or γ-radionuclide, may be performed shortly before the administration.

The CHELATES OF THE INVENTION may be suitable for imaging or treating various types of solid or non-solid tumors and metastases thereof, e.g. pituitary, gastroenteropancreatic, central nervous system, brain, breast, ovarian, colonic, prostate, kidney or lung cancer, paragangliomas, neuroblastomas, gliomas, medullary thyroid carcinomas, myelomas, bone tumors, carcinoids etc and metastases thereof.

For these uses, it is advantageous to choose, as the polypeptide moiety, such a compound as specifically accumulates at a particular organ or tissue of diagnostic or therapeutic target. According to the invention receptor-specific LIGANDS and CHELATES may be obtained for targetting a defined cell population.

According to a further aspect of the invention, there is provided:
   i. a pharmaceutical composition comprising a LIGAND OF THE INVENTION in free or in pharmaceutically acceptable salt form, together with one or more pharmaceutically acceptable carriers or diluents therefor;
   ii. a pharmaceutical composition comprising a CHELATE according to the invention in free or in pharmaceutically acceptable salt form, together with one or more pharmaceutically acceptable carriers or diluents therefor.
   iii. use of a LIGAND OF THE INVENTION in free or in pharmaceutically acceptable salt form, in the preparation of a diagnostic agent for imaging target tissues.

Such compositions may be manufactured in conventional manner. Preferably they are in liquid forms.

A composition according to the invention may also be presented in separate package with instructions for mixing the LIGAND with the metal ion and for the administration of the resulting CHELATE. It may also be presented in twin-pack form, that is, as a single package containing separate unit dosages of the LIGAND and the detectable metal ion with instructions for mixing them and for administration of the CHELATE. A diluent or carrier may be present in the unit dosage forms.

According to a further embodiment of the invention, compounds of formula XI

A—Z—R—Z₂   (XI)

wherein

A, Z and R are as defined above, and $Z_2$ is COOH or a functional group of a carboxy function, e.g. ($C_{1-12}$alkoxy) carbonyl are new and form part of the invention.

Preferred compounds of formula XI are those wherein A is derived from EDTA, DTPA or DOTA, particularly DTPA. Z is preferably —NH—. R is preferably $C_{1-4}$alkylene, particularly ethylene, —CH($R_5$)— as defined above or a radical of formula ($\alpha_2$) wherein ring A is unsubstituted.

Compounds of formula XI may be prepared in accordance with known methods. For example a polyamino polycarboxylic chelating agent may be reacted, preferably in the form of a dianhydride, with the bridging or spacer-yielding compound in an aqueous medium. The pH may conveniently be adjusted to slightly acidic.

Compounds of formula XII

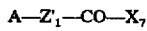

A—Z'₁—CO—X₇   (XII)

wherein

A is as defined above,

Z'₁ is either a direct bond or —Z—R— wherein Z and R are as defined above, and $X_7$ is —NH—NH₂ in protected or unprotected form or —N₃, are also novel and form part of the invention.

Preferably each of A, Z and R independently has one of the preferred significances as indicated above, respectively.

Compounds of formula XII may be prepared in accordance with known methods. They may be prepared by reacting either a compound of formula XI or a chelating agent bearing a reactive —COOH or a functional derivative thereof with hydrazine or a derivative thereof and then converted into the corresponding azide, e.g. as disclosed thereafter. Hydrazine is preferably used with one amino group being in protected form. The reaction may conveniently be performed in water or in a mixture of water and an alcohol, e.g. methanol, at a moderate temperature such as between cooling and slight heating, for example at room temperature, e.g. for one hour to 30 hours. If required the compounds of formula XII may be isolated and purified using any known purification methods such as chromatography.

In the following examples, all temperatures are in ° C. and $[\alpha]_D^{20}$-values uncorrected. The following abbreviations are employed:

Boc=tert.-butoxycarbonyl
TFA=trifluoroacetic acid
DTPA=diethylenetriamine-pentaacetic acid
DMF=dimethyl formamide The factor "F" shows the peptide content in the products obtained (F=1 conforms with 100 % peptide content). The difference up to 100 % [(1−1/F)×100] consists of acetic acid and water.

EXAMPLE 1

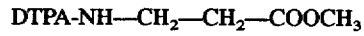

DTPA-NH—CH₂—CH₂—COOCH₃

5 g sodium bicarbonate and 2.1 g H₂N—CH₂—CH₂—CO—OCH₃, HCl are dissolved in 30 l water. After addition of 5.3 g DTPA-dianhydride and after 1 min reaction time the pH of the mixture is adjusted to 3 with HCl and then to 5.5 with NaOH 1N. The resulting mixture is freeze dried and then purified by chromatography eluting first with a mixture 7/4/2 and then with a mixture 7/5/4 of chloroform/methanol/ 50% acetic acid, to yield the title compound.

MH⁺: 479 (FAB-MS)

EXAMPLE 2

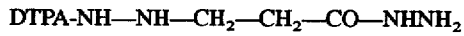

DTPA-NH—NH—CH₂—CH₂—CO—NHNH₂

200 mg hydrazine hydrate are added to a methanolic solution of 330 mg DTPA-NH—CH₂—CH₂—CO—OCH₃. After 24 hours at room temperature, the methanol is evaporated and the residue is chromatographed on silica gel using as eluant a mixture of 5/8/3 chloroform/glacial acetic acid/ water. The resulting product is further purified on an ion exchange resin (AG 4-X₄, OH-Form; Biorad). The title compound is obtained as a white lyophilisate.

MH⁺: 479 (FAB-MS)

EXAMPLE 3

DTPA-β-Ala-mEGF a) Preparation of the azide 14.3 mg DTPA-β-Ala-hydrazide are dissolved in 1 ml DMF and cooled to −15° C. 0.02 ml 3N HCl in diethylether and 5.4 μl tert.-butyl nitrite are then added to this solution. After 30 minutes, the resulting solution can be used for the next step (mother-liquor contains 0.03 mMol azide/ml solution).

b) Coupling 3 mg mEGF (1-53) are dissolved in 1 ml DMF and cooled to 0° C. To this solution are added 0.88 μl N-ethyl diisopropylamine and then 25 μl of the solution obtained in a). The resulting mixture is allowed to stay for 16 hours in the refrigerator. The progress of the reaction is tested by thin layer chromatography (eluant: 7/5/4 of chloroform/ methanol/50% acetic acid) and further 0.88 μl N-ethyl diisopropylamine and 25 μl azide solution obtained in a) are added to the mixture. After a further period of 12 hours in the refrigerator, the mixture is evaporated in vacuo and the residue is purified by reversed phase HPLC (column: ET 250/8/4 NUCLEOSIL 300-7 C18; Macherey and Nagel).

F=0.91

| Amino acid analysis: | Th. | Found |
|---|---|---|
| ASX | 7 | 7, 1 |
| GLX | 3 | 3, 2 |
| SER | 6 | 5, 3 |
| HIS | 1 | 0, 9 |
| THR | 2 | 1, 6 |
| beta-ALA | 1 | 1, 1 |
| ARG | 4 | 4, 0 (Standard) |

| Amino acid analysis: | Th. | Found |
|---|---|---|
| TYR | 5 | 5, 1 |
| CYS—CYS | 6 | 3, 2 |
| VAL | 2 | 1, 8 |
| MET | 1 | 1, 3 |
| ILE | 2 | 2, 2 |
| LEU | 4 | 4, 4 |
| PRO | 2 | 1, 9 |

EXAMPLE 4

$^{111}$In labeled DTPA-β-Ala-mEGF 1 mg DTPA-β-Ala-mEGF is dissolved in 0.01M acetic acid. The resulting solution is passed through a 0.22µ Millex-GV filter. $^{111}$InCl$_3$, Amersham, 370 MBq/ml) is prediluted in an equal volume of 0.5M sodium acetate. Labeling is carried out by mixing DTPA-β-Ala-mEGF with the InCl$_3$ solution and gentle mixing at room temperature.

EXAMPLE 5

$^{90}$Y labeled DTPA-β-Ala-mEGF $^{90}$Y is obtained from a $^{90}$Sr-$^{90}$Y radionuclide generator. The construction of the generator, its elution and the conversion of the [$^{90}$Y]EDTA to the acetate complex are performed in accordance with the method disclosed by M. Chinol and D. J. Hnatowich in J. Nucl. Med. 28, 1465–1470 (1987). 1 mg of DTPA-β-Ala-mEGF dissolved in 5 ml 0.01M acetic acid is allowed to warm to room temperature and 1.0 mCi of $^{90}$Y in 50 µl sterile 0.5M acetate is added. The mixture is then left undisturbed for 30 min to 1 hr to maximize chelation.

EXAMPLE 6

[DTPA-β-Ala-Trp$^{14}$]-Tetragastrin

By following the procedure of Example 3 (preparation of the azide and coupling) but using H-Trp-Met-Asp-Phe-NH$_2$ instead of mEGF, the title compound is obtained.

$[\alpha]_D^{20}$=−6,7° (c=0.5 in 95% AcOH) F=0.77

The title compound is then labeled with $^{111}$In or $^{90}$Y according to the procedure of Example 4 or 5 respectively.

EXAMPLE 7

[DTPA-β-Ala-Phe$^{B1}$]-bInsuline

By following the procedure of Example 3 but using A$^1$,B$^{29}$-Di-Boc-Insuline instead of mEGF and removing the protecting group with 100% CF$_3$COOH according to known method, the title compound is obtained.

F=0.83

The title compound is then labeled with $^{111}$In or $^{90}$Y according to the procedure of Example 4 or 5 respectively.

EXAMPLE 8

Acetyl-DPhe(pCl)-DPhe(pCl)-DTrp-Ser-Tyr-DLys (R)-Leu-Arg-Pro-DAla-NH$_2$

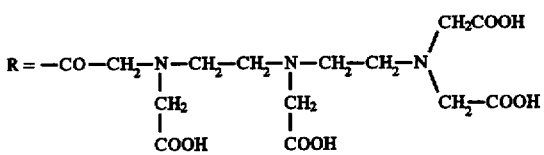

150 mg DTPA-hydrazide in 25 ml DMF are cooled to −20°. To this mixture are added 0.37 ml 3N HCl in ether and then 72 µl t.-butyl nitrite and the resulting mixture is stirred for ca. 30 min while the temperature is maintained from −15° to −20°. Thereafter a solution of 200 mg of acetyl-DPhe(pCl)-DPhe(pCl)-DTrp-Ser-Tyr-DLys-Leu-Arg-Pro-DAla-NH$_2$ in 100 ml DMF cooled to −20° is added followed by the addition of N-ethyl-diisopropylamine until pH 9 is obtained. The resulting mixture is stirred for ca. 70 hours at 0° while keeping the pH at 9.

DMF is then removed in vacuo until a final volume of 5 ml is left and the title compound is precipitated by addition of ether. The precipitate is filtered, washed and dried.

For purification, the title compound is dissolved in 150 ml water, the solution is adjusted to pH 7 by addition of NH$_4$OH, adsorbed on a duolite ES 881 column and eluted using a gradient of H$_2$O-Dioxane-AcOH. The fractions containing the title compound are collected and then lyophilized.

$[\alpha]_D^{20}$=−14.5° (c=0.2 in 95% AcOH)

The starting compounds may be prepared as follows:

a. DTPA-Hydrazide 2 g sodium bicarbonate are dissolved in 7 l water. To this solution are added 0.74 g BocHN-NH$_2$ and then 2 g DTPA dianhydride. After a few seconds a clear solution is obtained. The mixture is then evaporated at 40° to a volume of 0.5 l which is adjusted to pH 5 (max.) with 1N HCl. After stirring for 15 minutes, the mixture is adjusted to pH 7 with 1N NaOH and then lyophilized. Thereafter the product is chromatographied on silica gel using as eluant a mixture of chloroform, methanol, water and AcOH. The monosubstituted product is collected and further purified on an ion exchange resin (AG 4-X4, OH-Form; Biorad). The resulting product is dissolved in 10 ml TFA, the mixture is stirred for 30 minutes. DTPA-hydrazide is precipitated by addition of diisopropyl ether, filtered and dried under high vacuo.

b. Acetyl-DPhe(pCl)-DPhe(pCl)-DTrp-Ser-Tyr-DLys-Leu-Arg-Pro-DAla-NH$_2$

This peptide is synthesized on a mild acid cleavable resin [e.g. 4-(2',4'-dimethoxyphenyl-aminomethyl)-phenoxymethylpolystyrene, 1% crosslinked; available from e.g. Novabiochem] using N-α-Fmoc protected aminoacids which are added in the following order:

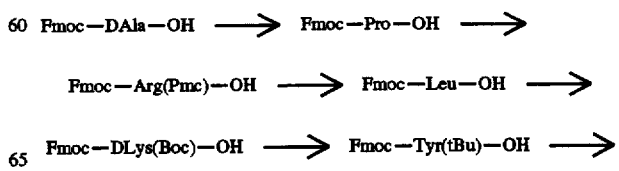

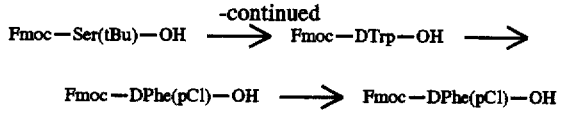

In each cycle the aminoacids are activated with diisopropylcarbodiimide/HOBt in DMF and, after complete coupling, the Fmoc-groups cleaved with 20% piperidine in DMF. N-acetylation in the last step is performed with acetic acid anhydride.

The protected peptide-resin is treated with TFA/H$_2$O (95:5) in order to simultaneously remove side chain protecting groups and liberate the peptide. Purification is achieved with RP-HPLC followed by ion-exchange on AG-4X$_4$, acetate. The title compound is thus obtained.

The title compound is then labeled with $^{111}$In or $^{90}$Y according to the procedure of Example 4 or 5 respectively.

EXAMPLE 9

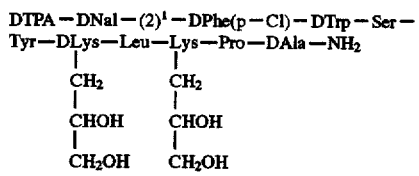

By following the procedure of Example 8 (preparation of the azide and coupling) but using H-DNal(2)$^1$-DPhe(p-Cl)-DTrp-Ser-Tyr-DLys(CH$_2$—CHOH—CH$_2$OH)-Leu-Lys(CH$_2$—CHOH—CH$_2$OH)-Pro-DAla-NH$_2$ as starting material, the title compound is obtained.

F=0.83

The starting peptide may be prepared by the solid phase synthesis procedure, e.g. as disclosed in Example 8b, but using Fmoc-DLys(CH$_2$—CHOH—CH$_2$OH) in cycles 3 and 5, Fmoc-DNal-OH is used in the last cycle. After complete coupling the protected peptide-resin is treated with TFA/H$_2$O (95:5) in order to simultaneously remove side chain protecting groups and liberate the peptide. The peptide is purified by RP-HPLC followed by ion-exchange on AG-4X$_4$, acetate.

$[\alpha]_D^{20}=-16°$ (c=0.5 in 95 % AcOH)

The title compound is then labelled with $^{111}$In or $^{90}$Y according to the procedure of Example 4 or 5 respectively.

EXAMPLE 10

Acetyl-His-Trp-Ala-Val-DAla-Lys(β-Ala-DTPA)-Leu-OEt

By following the procedure of Example 3 (preparation of the azide and coupling) but using Acetyl-His-Trp-Ala-Val-DAla-Lys-Leu-OEt as starting material, the title compound is obtained.

The starting peptide may be prepared as disclosed in EP-315 367-A.

The title compound is then labelled with $^{111}$In or $^{90}$Y according to the procedure of Example 4 or 5 respectively.

The affinity of the CHELATES OF THE INVENTION to the receptors present in the tumors may be assayed as follows:

EXAMPLE 11

BINDING PROPERTIES

An EGF receptor positive human tumor is removed and immediately stored at −70° C. During the subsequent isolation procedure this material is kept at 0° to 4° C. The tumor tissue is dissected into small cubes prior to homogenisation in 5 parts of Buffer A (20 mM HEPES, 0.1 mM EDTA and 250 mM sucrose, pH 7.4). Membranes are isolated by differential centrifugation. The material is then diluted in the incubation buffer containing 30 mM HEPES, pH 7.4, 1 mg/ml BSA and 1 mM benzamidine. The test mixture (200 µl final volume) contains 100 000 cpm [$^{125}$I]-EGF, the tissue (5 to 25 µg protein/assay) and compound of Example 3 at a concentration of 10$^{-9}$M. After mixing the icecold test solution on a vortex the tubes (polypropylene) are transfected to a waterbath and incubated for 30 min at 37° C. The reaction is stopped by addition of icecold Hank's or Tris buffer (4ml). The Tris buffer contains 10 mM Tris in 0.9% sodium chloride solution and is adjusted to pH 7.4. Routinely, filtration buffers contain 1% BSA (Fraction V) to suppress non-specific binding to the glass fiber filters (type A/E) that have been soaked in the filtration buffer a few minutes prior to use. The tubes are rinsed with 4 ml of the filtration buffer and the rinsing fluid is put over the respective filters. A third wash of the filters is followed by drying and the measurement of the filter-bound radioactivity in a γ-counter. The washing of the filters takes approximately 10 sec. It is observed that compound of Example 3 inhibits specifically bound [$^{125}$I]-EGF (IC$_{50}$=1.3 nM).

A similar binding assay procedure is repeated but using 1 µg of the compound of Example 3 labelled with 0.2 mCi $^{111}$InCl$_3$ as test substance. The tests are performed in siliconized borosilicate glass tubes and controls containing additionally 10$^{-7}$M EGF to determine non-specific binding are used. In these assays it is observed that the compound of Example 4 binds with high affinity to the EGF-receptors (IC$_{50}$=3 nM).

By following a similar binding assay procedure but using LHRH receptor positive anterior pituitary membranes from male Sprague-Dawley rats, 1 µg of the compound of Example 8 labelled with 0.4 mCi $^{111}$InCl$_3$ (labelling performed at room temperature for 15 minutes) and 10$^{-6}$M (DAla$^6$)LHRH for the determination of the non-specific binding, it is observed that $^{111}$In labelled compound of Example 8 binds with high affinity to the LHRH-receptors (IC$_{50}$=1.1 nM).

EXAMPLE 12

BIODISTRIBUTION

Biodistribution of radioactivity may be determined either with standard imaging techniques in nude mice weighing 20+5 g and bearing an EGF receptor positive rumour (MDA 231, MDA 468 or A 431 tumors) or through serial sacrifice of a number of such animals and determination of the organ radioactivity. Compound of Example 4 is administered i.v. to the animals at a dosage corresponding to 90–100 µCi and the radioactivity is assessed 5 min, 10 min, 15 min, 30 min, 60 min, 20 hrs and 48 hrs. 5 minutes after injection, radioactivity is detected in the liver, kidneys, urinary bladder and in the tumor site. Radioactivity is increasing and is localized on the tumor site 60 min after injection. EXAMPLE 13

DTPA-mEGF

By following the procedure of Example 8 but using mEGF as starting material, the title compound is obtained.

The title compound is then labelled with $^{111}$In or $^{90}$Y according to the procedure of Example 4 or 5 respectively.

EXAMPLE 14

1-(p-isothiocyanatobenzyl)-DTPA-mEGF

To a solution of 3 mg of mEGF in 5 ml acetonitrile/water (1/1 v/v), which is adjusted to pH 9.8 with NA$_2$CO$_3$, 1,5 mg of N-{2-[bis(carboxymethyl)amino]ethyl}-N'-{2-bis-[bis(carboxymethyl)amino]-2-(p-isothiocyanato-benzyl)-ethyl}-glycine [or 1-(p-isothiocyanatobenzyl)-DTPA] are added. After a reaction time of 9 hours at room temperature the solution is diluted with water to 20 ml and loaded on to RP-HPLC column. The title compound is isolated by gradient elution (buffer A: 0.11 trifluoroacetic acid, buffer B: 0.1% trifluoroacetic acid in acetonitrile) and obtained as white lyophilisate after freeze drying.

The title compound is then labelled with $^{111}$In or $^{90}$Y according to the procedure of Example 4 or 5 respectively.

EXAMPLE 15 p-isothiocyanatobenzyl-DOTA-mEGF

The title compound is obtained according to the procedure of Example 14 using p-isothiocyanatobenzyl-DOTA instead of 1-(p-isothio-cyanatobenzyl)-DTPA. The title compound is then labelled with $^{111}$In or $^{90}$Y according to the procedure of Example 4 or 5 respectively.

We claim:

1. A peptide in free base or salt form consisting of EGF having a chelating group capable of complexing with a detectable element covalently linked either directly or indirectly by means of a divalent bridging group to the N-terminal amino group or a lysine N$^\epsilon$-amino group of said EGF, the chelating group being selected from the group consisting of Diethylenetriamine pentaacetic acid;

N-hydroxyethyl-N,N',N'-ethylenediamine triacetic acid;

Ethylene glycol-O,O'-bis(2-aminoethyl)-N,N,N',N'-tetraacetic acid;

N,N'-bis(hydroxybenzyl)ethylenediamine-N,N'-diacetic acid;

Triethylenetetramine hexaacetic acid;

1,4,7,10-tetraazacyclododecane-N,N',N'',N'''-tetraacetic acid;

1,4,8,11-tetraazacyclotetradecane-N,N',N'',N'''-tetraacetic acid;

N'-p-isothiocyanatobenzyl-diethylenetriamine-N,N,N'', N''-tetraacetic acid;

N'-p-isothiocyanatophenethyl-diethylenetriamine-N,N, N'', N'''-tetraacetic acid;

N-{2-[bis(carboxymethyl)amino]ethyl}-N'-{2-[bis(carboxymethyl)amino]-2-(p-isothiocyanatobenzyl)-ethyl}-glycine; a compound of formula Ia, Ib or Ic, (Ia)

(Ib)

(Ic)

wherein $R_{10}$ is —CH$_2$COOH, and $R_{11}$ is —(CH$_2$)$_{1-6}$—NCS, p-isothiocyanatobenzyl, or p-isothiocyanatophenethyl;

and a compound of formula v (V)

wherein each of $R_{24}$, $R_{25}$, $R_{26}$, $R_{27}$, $R_{28}$ and $R_{29}$ is independently hydrogen or C$_{1-4}$alkyl, m' is 2 or 3, and X$_2$ is p-isothiocyanatobenzyl or p-isothiocyanatophenethyl.

2. A peptide according to claim 1 wherein the chelating group is attached indirectly by means of a divalent bridging group to the amino group.

3. A peptide according to claim 1 wherein the chelating group is attached by an amide bond to the amino group.

4. A peptide according to claim 1 wherein the divalent bridging group is a radical of formula ($\alpha_1$)

—Z—R—CO—  ($\alpha_1$)

wherein

R is C$_{1-11}$alkylene, hydroxy substituted C$_{2-11}$alkylene, C$_{2-11}$alkenylene, $$-\underset{R_5}{\overset{|}{CH}}-,$$

cyclohexylene, substituted cyclohexylene, or a radical of formula ($\alpha_2$)

($\alpha_2$)

wherein n and m are each independently 0, 1, 2, or 3 and $R_5$ is a residue as attached in C$\alpha$ of a natural or synthetic $\alpha$-amino acid, and Z is a divalent group capable of covalently reacting with the chelating agent.

5. A peptide according to claim 1 wherein the chelating group is attached to the N-terminal amino group.

6. A peptide according to claim 1 wherein the chelating group is attached to a lysine N$^\epsilon$-amino group of EGF.

7. A peptide according to claim 1 in free form or in pharmaceutically acceptable salt form.

8. A pharmaceutical composition comprising a peptide of claim 1 in free form or in pharmaceutically acceptable salt form in association with a pharmaceutically acceptable carrier or diluent.

9. The peptide of claim 1, which is diethylenetriamine pentacetic acid-β-Ala-mEGF".

10. The peptide according to claim 1 which is diethylenetriamine pentacetic acid-mEGF.

11. The peptide according to claim 1 which is p-isothiocyanatobenzyl-diethylenetriamine pentaacetic acid-mEGF.

12. The peptide according to claim 1 which is p-isothiocyanatobenzyl-1,4,7,10-tetraazacyclododecane-N,N',N",N'"-tetraacetic acid-mEGF.

13. A chelate in free base or pharmaceutically acceptable acid addition salt form consisting of an EGF peptide having a chelating group complexed with a detectable element covalently linked either directly or indirectly by means of a divalent bddging group to the N-terminal amino group or a lysine $N^\epsilon$-amino group of said EGF peptide, the chelating group being selected from the group consisting of
Diethylenetriaminepentaacetic acid;
N-hydroxyethyl-N,N',N'-ethylenediaminetriacetic acid;
Ethylene glycol-)O,O'-bis(2-aminoethyl)-N,N,N',N'-tetraacetic acid;
N,N'-bis(hydroxybenzyl)ethylenediamine-N,N'-diacetic acid;
Triethylenetetraminehexaacetic acid;
1,4,7,10-tetraazacyclododecane-N,N',N",N'"-tetraacetic acid;
1,4,8,11-tetraazacyclotetradecane-N,N',N",N'"-tetraacetic acid;
N'-p-isothiocyanatobenzyl-diethylenetriamine-N,N,N",N"-tetraacetic acid;
N'-p-isothiocyanatophenethyl-diethylenetriamine-N,N',N",N'"-tetraacetic acid;
N-{2-[bis(carboxymethyl)amino]ethyl}-N'-{2-[bis(carboxymethyl)amino]-2-(p-isothiocyanatobenzyl)ethyl}-glysine;

a compound of formula Ia, Ib or Ic

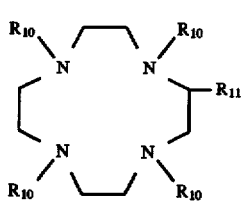

(Ia)

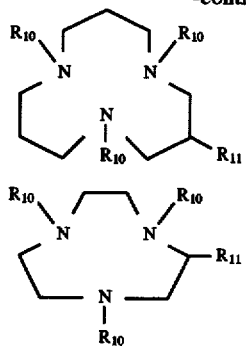

wherein $R_{10}$ is —$CH_2COOH$, and $R_{11}$ is —$(CH_2)_{1-6}$—NCS, p-isothiocyanatobenzyl, or p-isothiocyanatophenethyl;

and a compound of formula V

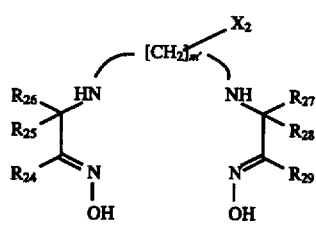

wherein each of
$R_{24}$, $R_{25}$, $R_{26}$, $R_{27}$, $R_{28}$ and $R_{29}$ is independently hydrogen or $C_{1-4}$alkyl,
m' is 2 or 3, and
$X_2$ is p-isothiocyanatobenzyl or p-isothiocyanatophenethyl.

14. A chelate according to claim 12 wherein the detectable element is a fluorescent or a α-, β- or γ-emitting element.

15. A pharmaceutical composition comprising a chelate according to claim 13 in free form or in pharmaceutically acceptable salt form in association with a pharmaceutically acceptable carrier or diluent.

16. The chelate according to claim 13 which is $^{111}$In labeled diethylenetriamine pentaacetic acid-β-Ala-mEGF.

17. The chelate according to claim 13 which is $^{90}$Y labeled diethylenetriamine pentaacetic acid-β-mEGF.

* * * * *